(12) United States Patent
LaFontaine

(10) Patent No.: US 7,875,054 B2
(45) Date of Patent: Jan. 25, 2011

(54) CONNECTIVE TISSUE CLOSURE DEVICE AND METHOD

(75) Inventor: Daniel M. LaFontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 711 days.

(21) Appl. No.: 11/865,140

(22) Filed: Oct. 1, 2007

(65) Prior Publication Data
US 2009/0088794 A1   Apr. 2, 2009

(51) Int. Cl.
*A61B 17/08* (2006.01)
*A61D 1/00* (2006.01)

(52) U.S. Cl. ..................................... 606/213
(58) Field of Classification Search ........... 606/213, 606/215–218, 232; 27/136 R; 128/898
See application file for complete search history.

(56) References Cited

U.S. PATENT DOCUMENTS

| | | | | |
|---|---|---|---|---|
| 4,259,959 A | * | 4/1981 | Walker | 606/221 |
| 5,234,448 A | * | 8/1993 | Wholey et al. | 606/153 |
| 5,254,127 A | * | 10/1993 | Wholey et al. | 606/153 |
| 5,383,897 A | * | 1/1995 | Wholey | 606/213 |
| 5,478,353 A | * | 12/1995 | Yoon | 606/213 |
| 5,645,566 A | * | 7/1997 | Brenneman et al. | 606/213 |
| 5,782,861 A | * | 7/1998 | Cragg et al. | 606/216 |
| 5,910,155 A | * | 6/1999 | Ratcliff et al. | 606/213 |
| 5,919,207 A | * | 7/1999 | Taheri | 606/219 |
| 5,964,782 A | * | 10/1999 | Lafontaine et al. | 606/213 |
| 5,976,174 A | | 11/1999 | Ruiz | |
| 6,077,281 A | | 6/2000 | Das | |
| 6,080,182 A | | 6/2000 | Shaw et al. | |
| 6,120,524 A | | 9/2000 | Taheri | |
| 6,206,907 B1 | | 3/2001 | Marino et al. | |

(Continued)

FOREIGN PATENT DOCUMENTS

EP    1 595 504 A1    11/2005

(Continued)

OTHER PUBLICATIONS

Article entitled "Novel Properties of PLA Fibers" authored by Jeffrey S Dugan, dated Jan. 2000.

(Continued)

*Primary Examiner*—(Jackie) Tan-Uyen T Ho
*Assistant Examiner*—Dianne Dornbusch
(74) *Attorney, Agent, or Firm*—Seager, Tufte & Wickhem, LLC

(57) ABSTRACT

A device for closing wounds such as openings in blood vessels as well as a method of doing so are disclosed. The device employs a fabric wrapped around an expandable frame both of which are inserted into a blood vessel through an introducer sheath. Once inserted, the expandable frame expands thereby expanding the fabric therewith. The fabric is made from a bioabsorbable material and includes a plurality of microhooks extending therefrom. One suitable material is polylactic acid fiber. Upon retraction of the device, the microhooks engage the adventitia surrounding the blood vessel causing the fabric to remain in position sealing the opening even after the expandable member is retracted and removed as well as the introducer sheath As the fabric is made from a bioabsorbable material, the device can remain in place even after hemostasis is reached and eventually dissolve within the body.

7 Claims, 7 Drawing Sheets

U.S. PATENT DOCUMENTS

| | | | |
|---|---|---|---|
| 6,270,515 B1 | 8/2001 | Linden et al. | |
| 6,290,674 B1* | 9/2001 | Roue et al. | 604/107 |
| 6,524,326 B1* | 2/2003 | Zhu et al. | 606/213 |
| 6,537,299 B1* | 3/2003 | Hogendijk et al. | 606/213 |
| 6,537,300 B2* | 3/2003 | Girton | 606/213 |
| 6,547,806 B1* | 4/2003 | Ding | 606/213 |
| 6,893,431 B2* | 5/2005 | Naimark et al. | 604/891.1 |
| 7,160,312 B2* | 1/2007 | Saadat | 606/153 |
| 7,510,560 B2* | 3/2009 | Manzo | 606/153 |
| 2002/0026215 A1* | 2/2002 | Redmond et al. | 606/213 |
| 2003/0073979 A1* | 4/2003 | Naimark et al. | 604/891.1 |
| 2004/0068273 A1* | 4/2004 | Fariss et al. | 606/144 |
| 2004/0122349 A1* | 6/2004 | Lafontaine et al. | 604/11 |
| 2004/0220610 A1 | 11/2004 | Kreidler et al. | |
| 2005/0010248 A1* | 1/2005 | Lafontaine | 606/213 |
| 2005/0096498 A1 | 5/2005 | Houser et al. | |
| 2006/0106418 A1 | 5/2006 | Seibold et al. | |
| 2007/0049968 A1* | 3/2007 | Sibbitt et al. | 606/213 |
| 2007/0060895 A1* | 3/2007 | Sibbitt et al. | 604/215 |
| 2007/0203506 A1* | 8/2007 | Sibbitt et al. | 606/139 |
| 2009/0254119 A1* | 10/2009 | Sibbitt et al. | 606/213 |
| 2010/0130965 A1* | 5/2010 | Sibbitt et al. | 606/2 |

FOREIGN PATENT DOCUMENTS

| | | |
|---|---|---|
| WO | WO 98/27868 | 7/1998 |
| WO | 02/096295 A1 | 12/2002 |
| WO | WO 03/065898 | 8/2003 |
| WO | 2004/093649 A2 | 11/2004 |
| WO | WO 2005/115253 | 12/2005 |
| WO | WO 2006/078578 | 7/2006 |
| WO | 2007/025019 A2 | 3/2007 |

OTHER PUBLICATIONS

Hamann; European Patent Office; International Search Report; Aug. 22, 2005.

Grieb; European Patent Office; International Searching Authority; Jul. 8, 2008.

* cited by examiner

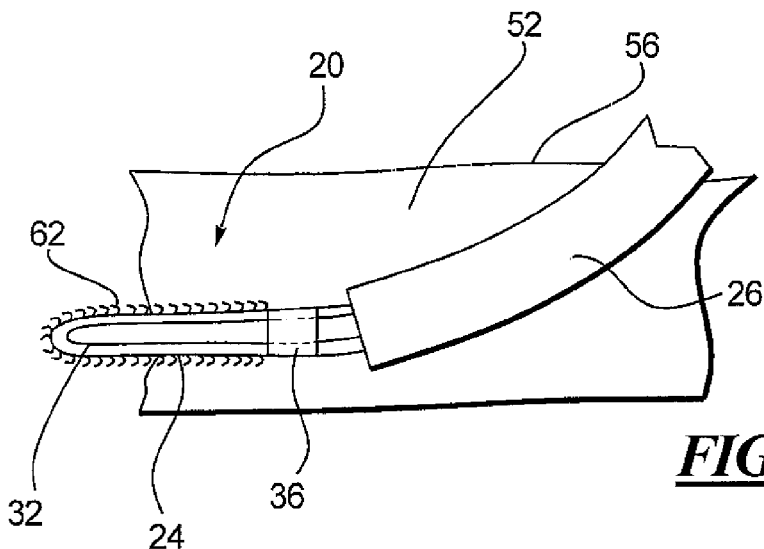
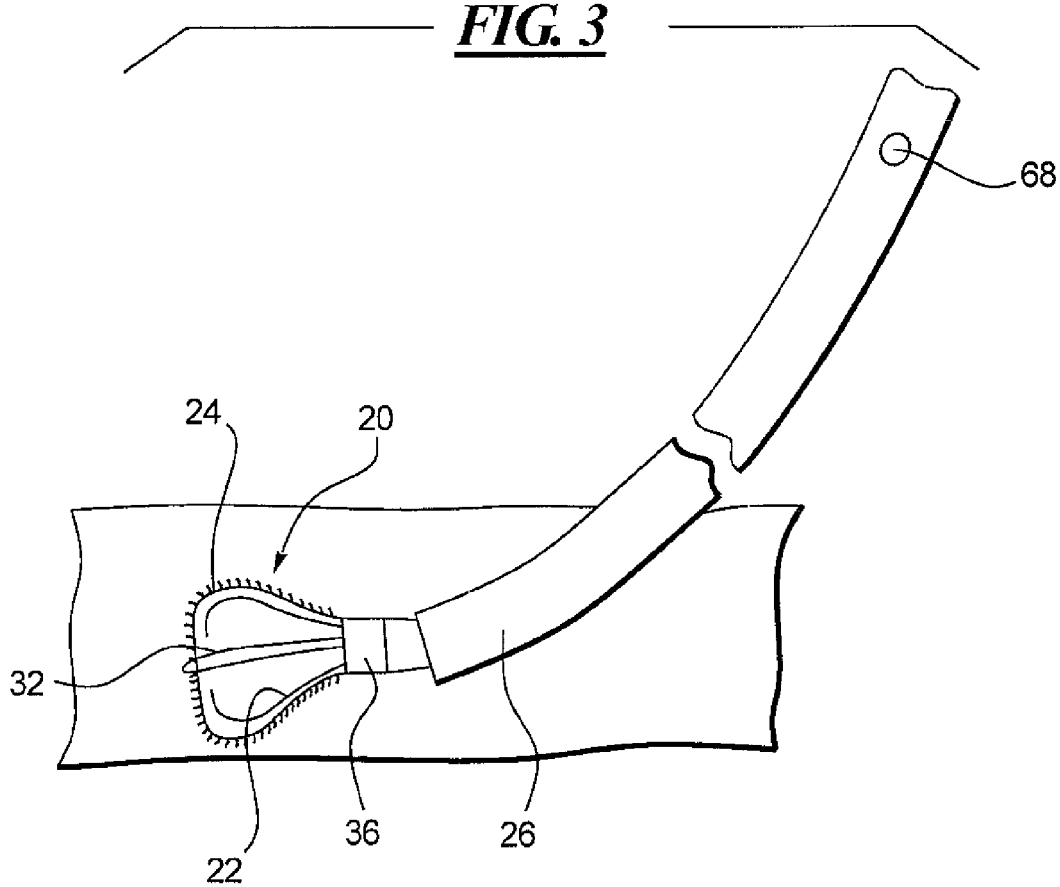

CONNECTIVE TISSUE CLOSURE DEVICE AND METHOD

FIELD OF THE DISCLOSURE

The present disclosure generally relates to medical devices, and more particularly, relates to devices for closing openings in blood vessels, wounds and the like.

BACKGROUND OF THE DISCLOSURE

In many medical procedures, including but not limited to angiography and stent implantations, it is necessary to make an incision in an artery of the body, typically the femoral artery, to allow for access into the vasculature, of a guidewire, catheter, balloon catheter, stent, navigational wire, or the like. Once that incision is made and the medical procedure is performed, the apparatus is all withdrawn from the vasculature and the opening in the femoral artery must be repaired.

Over time many devices and methods have been developed for doing so. Conventionally, mechanical compression is simply applied using hand pressure, weighted bags or similar structure, to apply sufficient pressure to the artery until hemostasis can be achieved. While effective, the process can be relatively slow, often taking up to 24 hours for a clot to be formed. In addition, during this time, the patient must remain stationary. In addition, the simple application of such pressure or weight is often of great discomfort to the patient, or can detrimentally affect other systems of the body due to the applied weight, pressure and immobility.

In other attempts, an anchor of some form is introduced into the blood vessel to serve as a back stop against which closure gels or structures can be pushed. For example, a balloon catheter can be introduced into the blood vessel, and expanded, and thereafter retracted until the balloon engages an inside surface of the blood vessel wall. At that point, a collagen plug, foam pledget, or similar structure can be tamped down against the balloon to form a seal. While this is also effective, such devices and methods do have the unfavorable disadvantage of positioning a portion of the closure within the blood vessel itself.

In still further devices and methods, it is known to close the opening in a blood vessel wall without leaving any foreign body behind after the procedure. For example, cautery devices can be used to heat the collagen within the blood so as to form a clot. Such cautery devices can use conventional heating methods or function through the introduction of radio frequency energy between first and second electrodes positioned proximate the blood vessel wall In other devices, ultrasonic energy can be directed to the blood vessel wall with the cells themselves being vibrated at a frequency sufficient to cause sufficient heat and hemostasis as well.

While these latter devices and methods can be effective, they are often difficult for the physician to execute, can cause pain to the patient, and can be relatively time consuming. Accordingly, it would be advantageous to provide an apparatus or method for closing the opening in the blood vessel which is immediate and relatively easy for the physician to execute, but which does so without leaving any structure behind, or at least using structure which is bioabsorbable after a relatively short period of time, thereby ultimately leaving no foreign substance in the body.

SUMMARY OF THE DISCLOSURE

In accordance of one aspect of the disclosure, a wound closure device is disclosed which comprises an expander adapted to move between expanded and contracted positions, and a fabric wrapped over the expander, the fabric being manufactured from polylactic acid fiber.

In accordance with another aspect of the disclosure, a method of closing a wound is disclosed comprising positioning an introducer sheath into a blood vessel, inserting a sealing assembly through the introducer sheath, the sealing assembly including an expandable frame surrounded by a tube of fabric, expanding the expandable frame, the fabric being expanded thereby as well, and retracting the sheath and sealing assembly until the sheath is removed from the artery. The fabric may include microhooks which become engaged with adventitia surrounding the blood vessel. After doing so, the expandable frame is contracted and removed thereby inverting the distal end of the fabric tube. A cinch ring is then slid down around the inverted end of the fabric tube. The sealing assembly includes an expandable frame surrounded by a tube of fabric. In addition, the tube has a closed distal end and a plurality of microhooks extending therefrom. The sealing assembly is inserted into the introducer sheath until the distal end of the tube extends from a distal end of an introducer sheath.

In accordance with another aspect of the disclosure, a wound closure device is disclosed comprising an introducer sheath having a distal end and a proximal end, an expandable frame slideably disposed within the introducer sheath, a fabric tube wrapped around the expandable frame, the fabric tube having a plurality of microhooks extending therefrom, the fabric tube being closed at a distal end, a cinch ring positioned around the fabric tube and expandable frame, a suture removably connected to the fabric tube distal end and extending through the introducer sheath to the proximal end, and a deployment mechanism connected to the introducer sheath distal end, the deployment mechanism adapted to expand and contract the expandable frame, retract the suture, and depress the cinch ring.

These and other aspects and features of the disclosure will become more apparent upon reading the following description when taken in conjunction with the accompanying drawings.

BRIEF DESCRIPTION OF THE DRAWINGS

FIG. 2 is a schematic representation of the device during a first step of being introduced into a blood vessel into a blood vessel;

FIG. 3 is a schematic view similar to FIG. 2, but showing a second step of expanding the device;

Figure 1:
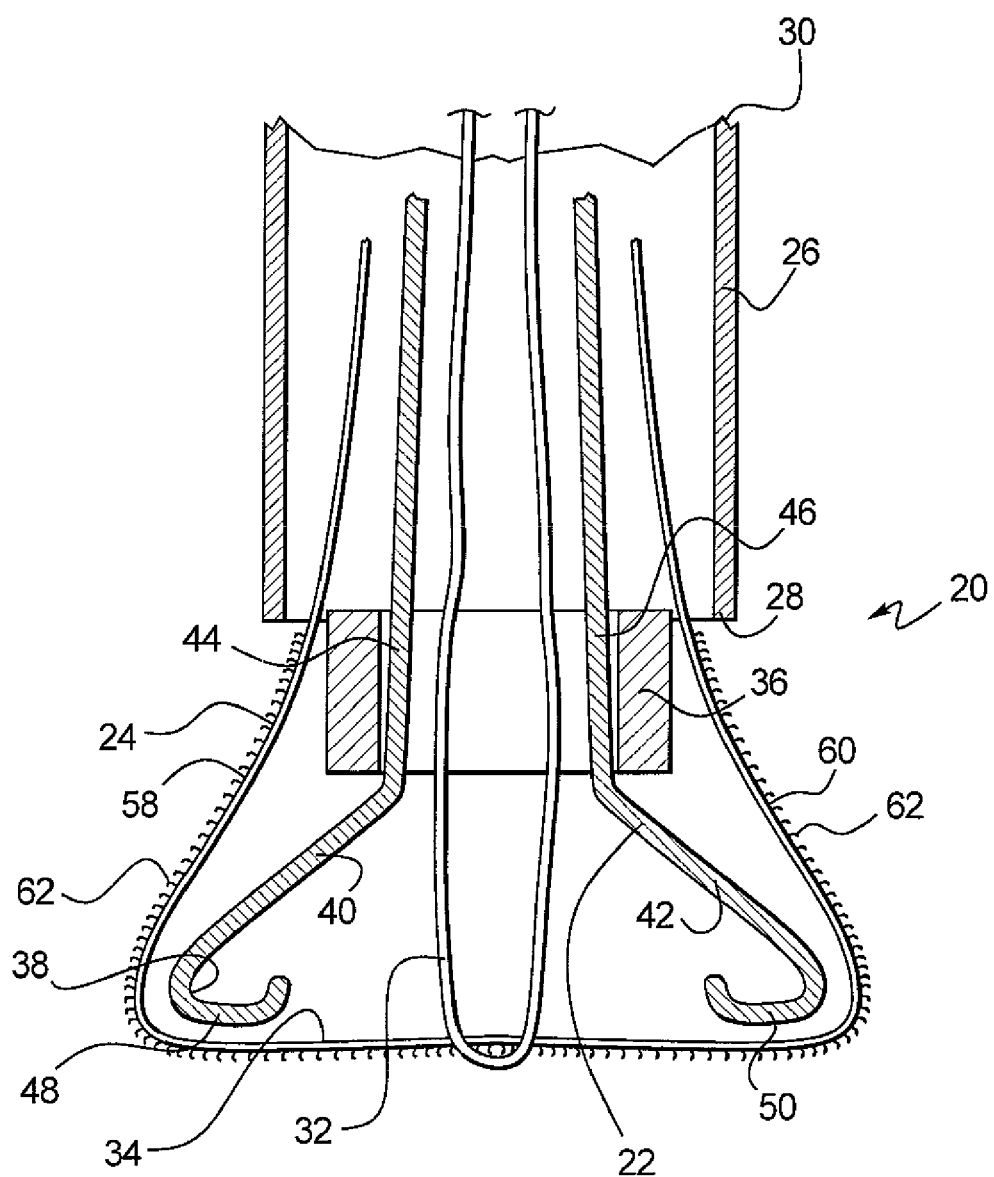
FIG. 1 is a sectional view of a wound closure device constructed in accordance with the teachings of the disclosure.

While the present disclosure is susceptible to various modifications and alternative constructions, certain illustrative embodiments thereof have been shown in the drawings and will be described below in detail. It should be understood, however, that there is no intention to limit the present invention to the specified forms disclosed, but on the contrary, the intention is to cover all modifications, alternative constructions, and equivalents falling within the spirit and scope of the present invention.

DETAILED DESCRIPTION OF THE DISCLOSURE

Referring to the drawings and with specific reference to FIG. 1, a wound closure device constructed in accordance with the teachings of the disclosure is generally referred to as reference numeral 20. It is to be understood that while the device 20 is described below in connection with the closure of an opening in a blood vessel such as a femoral artery, the teachings of this disclosure can be used to construct any number of medical devices including those for closure of larger openings in other vasculature, organs, or skin.

The device 20 is shown in partial cut-away view in FIG. 1 as including an expandable frame 22 around which is wrapped a fabric 24. In addition, both the expandable frame 22 and fabric 24 are shown to be slidably disposed within an introducer sheath 26 having a distal end 28 and a proximal end 30. Completing the structure depicted in FIG. 1, the device 20 further includes a suture 32 removably connected to a closed end 34 of the fabric 24, as well as a cinch ring 36 disposed around both the expandable frame 22 and suture 32.

Figure 12:
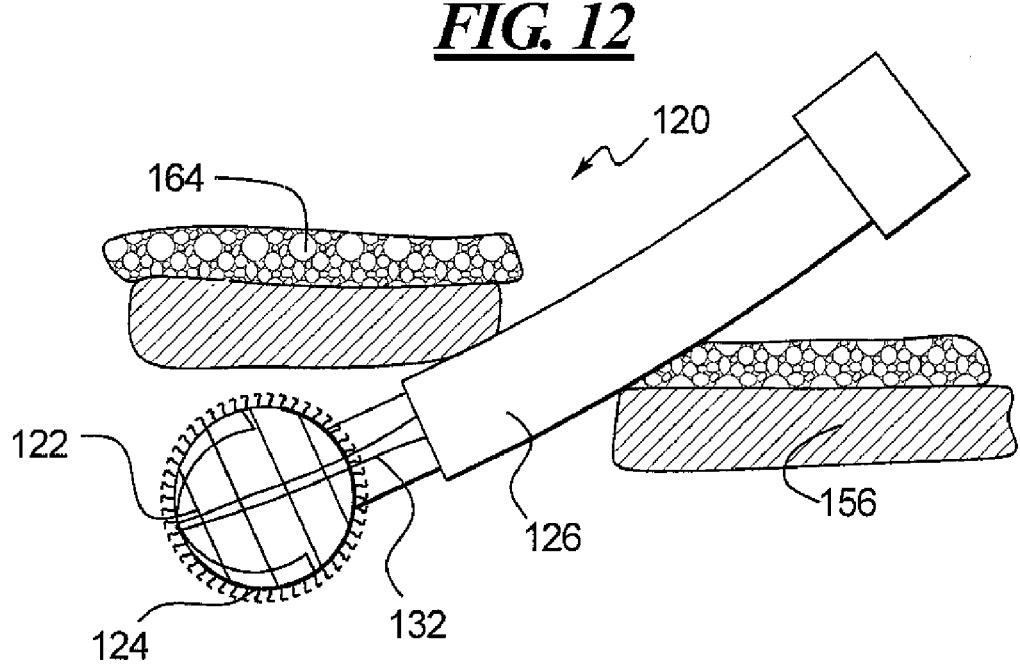
FIG. 12 is a perspective view depicting an alternative embodiment of the wound closure device with the distal end of the closure device being ball-like or spherical in shape.
Figure 13:
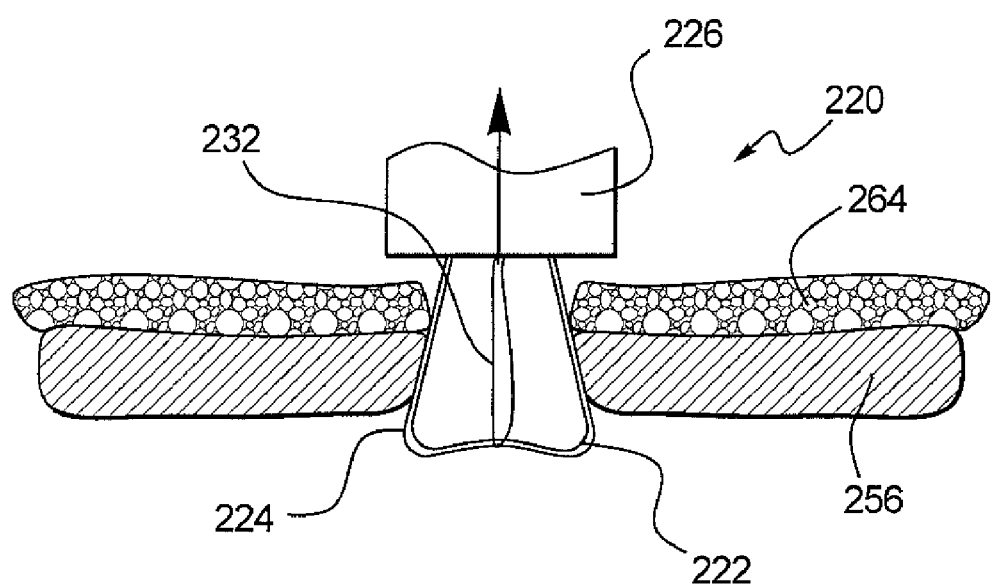
FIG. 13 is a perspective view of another alternative embodiment depicting a wound closure device distal end which is conical in shape.

With specific reference to the structure of the expandable frame 22, it can be provided in any number of forms with that depicted in FIGS. 1-10 being one example, and those depicted in FIGS. 12 and 13 being two other examples. It is to be understood that other shapes are certainly possible within the scope of this disclosure. However, in FIG. 1 the expandable frame 22 includes, at its distal end 38, first and second legs 40 and 42. First and second legs 40, 42 extend, respectively, from first and second spines 44 and 46 and terminate in first and second feet 48 and 50. As will be described in further detail herein, particularly with reference to FIGS. 3 and 6, the expandable frame 22 is readily moveable between expanded and contracted positions. The expandable frame 22 may be manufactured from memory metals such as the nickel-titanium alloy marketed under the trademark "NitinolTM" or the cobalt-chromium-nickel alloy marketed under the "ElgiloyTM" trademark, among others. In addition, the expandable member can be manufactured from an expandable or memory polymer, a balloon, a compressible foam, or the like.

With respect to the fabric 24, it is generally provided in the shape of a tube having a closed distal end 34 as indicated above. Additionally, and importantly, the fabric 24 includes a plurality of microhooks extending outwardly therefrom. One suitable material from which this fabric can be manufactured is polylactic acid (PLA) fiber. PLA fiber is defined as a substance composed of at least 85% by weight of lactic acid ester units derived from naturally occurring sugars. The PLA fibers are typically made using lactic acid as the starting material for polymer manufacture. The lactic acid comes from fermenting various sources of natural sugars. The sugars can come from annually renewable agricultural crops such as corn or sugar beans. The fundamental polymer chemistry of PLA allows control of certain fiber properties and makes the fiber suitable for a wide variety of applications in that it includes the following advantageous features: low moisture absorption and high wicking; low flammability and smoke generation; high resistance to ultraviolet light; low index of refraction; low specific gravity, it is readily meltspun; and most importantly to this disclosure, it is bioabsorbable. One suitable commercial source of PLA fiber mesh is that provided by Sofradim Corporation of Lyons, France.

While the foregoing disclosure is written in primary reference to polylactic acid, it is to be understood that other bioabsorbable materials and other materials can be used in constructing the present disclosure. Those materials include, but are not limited to, polypropylene (PPL), poly(glycolic acid) (PGA), polyethylene terephthalate (PET), nylon, and poly (trimethylene terephthalate) (PTT). The primary features of any of the selected materials must be the ability to be bioabsorbed by the human body over time, and the ability to be manufactured in mesh or fabric form having a plurality of the aforementioned microhooks. The microhooks may be provided in an extremely small dimension, for example, between 0.001 and 0.01 inches. Other dimensions are certainly possible.

Referring now to FIGS. 2-10, a method of deploying the closure device will be shown in detail. In a first step depicted in FIG. 2, the device 20 is inserted into a blood vessel 52 by way of an opening 54 (see FIG. 11) provided in the blood vessel wall 56. When inserting the device 20, the expandable frame 22 and surrounding fabric can be fully received in the introducer sheath 26 or extend therefrom as indicated in FIG. 2. Once fully inserted into the blood vessel, the expandable frame 22 is expanded as depicted in FIG. 3. In so doing the fabric 24 surrounding the frame 22 is expanded as well. If the device 20 uses a memory metal as the aforementioned Nitinol™ or Elgiloy™, the legs 42 will expand outwardly immediately upon being free to do so. In an alternative embodiment (not depicted), wherein a balloon serves as the expandable frame, pressurized liquid or gas can be injected into the balloon so as to expand the balloon and thereby expand the fabric as well. In addition, expandable mesh, expandable foam, or memory shaped polymer may be used for expansion of the hook fabric.

Figure 4:
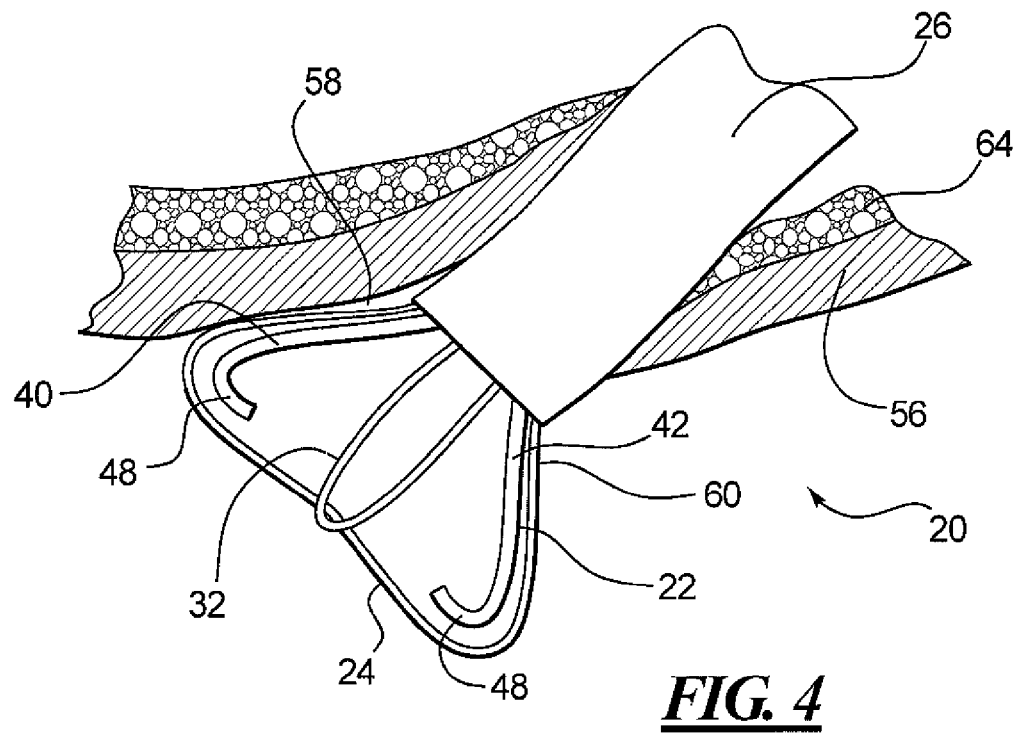
FIG. 4 is a schematic view similar to FIG. 2, but showing a third step of retracting the device.
Figure 5:
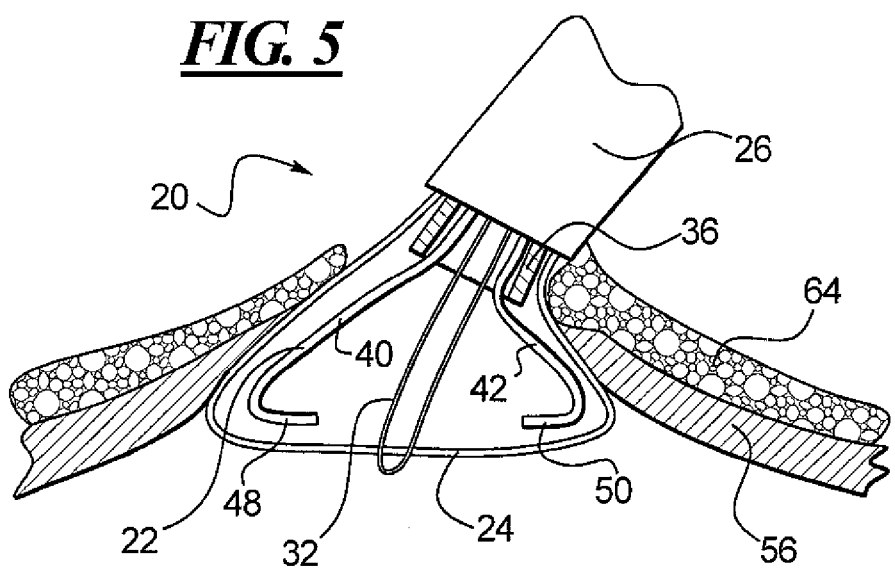
FIG. 5 is a schematic view showing a later step of the introducer sheath being pulled away, and the adventitia being engaged by the microhooks.

Once the expandable frame 22 is in this deployed configuration, the entire device 20 can be retracted out of the blood vessel as shown best in FIG. 4. However, as the frame 22 is expanded, the device does not freely pull out of the blood vessel but rather the tapered sides 58, 60 of the device 20 engage the interior surfaces of the blood vessel wall 56. Microhooks 62 extending from the fabric harmlessly slide over the tissue of the blood vessel wall 56, but upon further retraction, the microhooks 62 encounter the adventitia 64, the sinuous tissue immediately adjacent the outer surface 66 of the blood vessel wall 56. Upon doing so, the microhooks 62 are such that once they engage the adventitia and become tightly entangled therewith, they cannot be removed easily by further retractive force applied by the physician. Rather, as shown best in FIG. 5, the microhooks 62, engage with the adventitia 64, and cause the adventitia 64 to pull away with the device 20.

In so doing, it can be seen that the blood vessel wall 56, as well as adventitia 64, cone outwardly away from the blood vessel. This retraction is continued until the introducer sheath 26 is fully removed from the blood vessel 52. The physician knows this position has been reached in that the introducer sheath 26 is provided with a bleed back port 68. In other words, once the introducer sheath 26 is sufficiently removed from the blood vessel 52 so as to not be within the blood vessel, blood will no longer flow through the introducer sheath 26 and either blood flow out of the bleed back port 68 will completely stop, or it will at least cease to a degree indicating to the physician that the introducer sheath 26 has been fully removed from the blood vessel.

Figure 6:
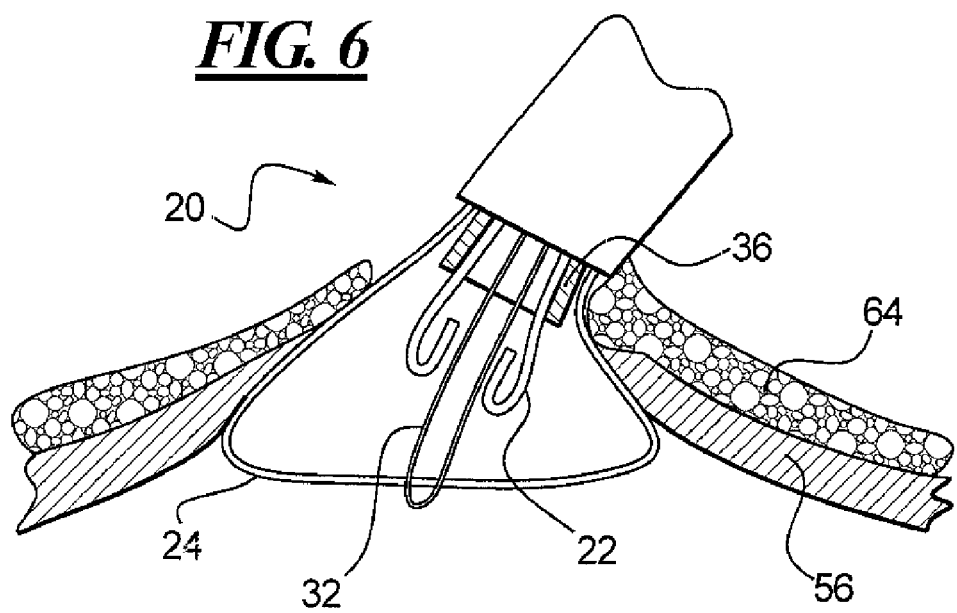
FIG. 6 is a schematic view depicting the expandable frame being contracted and retracted.

Referring now to FIG. 6, once this position of the introducer sheath 26 has been reached, the expandable frame 22 is contracted and retracted out of the blood vessel and out of the body. However, as the microhooks 62 are fully engaged with the adventitia 64, the fabric 24 remains within the blood vessel substantially sealing the opening 54 provided therein.

Simultaneously with the retraction of the expandable frame 22, the suture 32 is retracted as well. As the suture 32 is connected to the closed end 34 of the fabric 24, this causes the closed end 34 to invert as shown best in FIG. 7. Once inverted it can be seen that the peripheral ends 70 of the fabric 24 remain engaged with the adventitia 64 proximate the wound opening 54 with the interior section 72 of the fabric 24 creating a closed end tube 65 extending away from the blood vessel In addition, as the microhooks 62 are now positioned to face one another, they entwine with one another to prevent the closure device from reopening.

Figure 7:
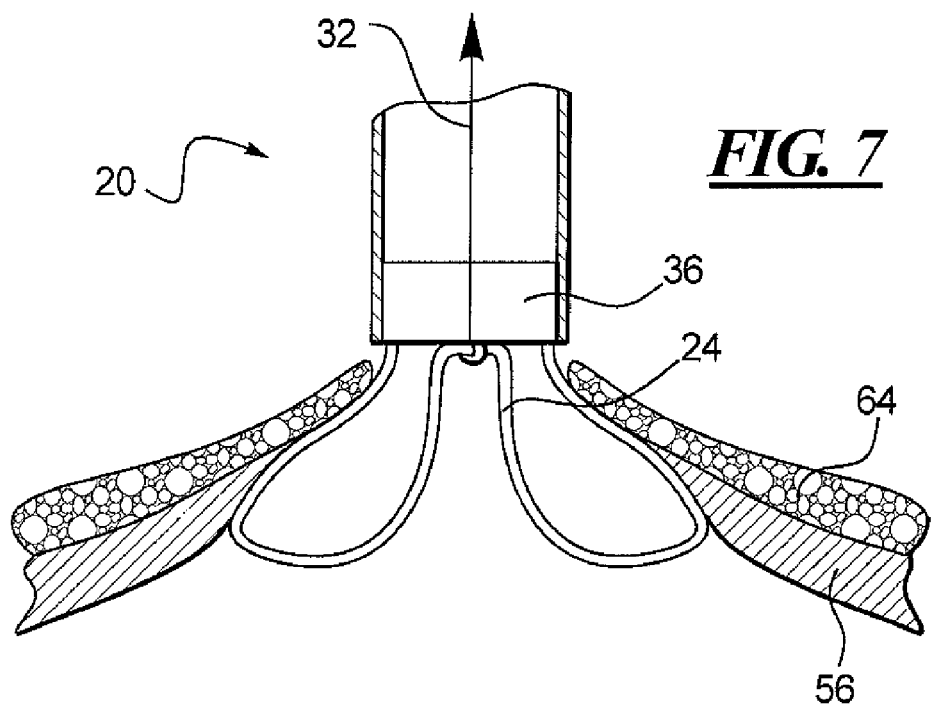
FIG. 7 is schematic view depicting the suture being retracted.

In order to further ensure that the device remains closed, the cinch ring 36 is subsequently deployed over the close end tube. This is best depicted in FIG. 7. The cinch ring 36, as indicated above, is manufactured from a bioabsorbable material, such as polylactic acid (PLA) fiber or the like. The ring includes an interior diameter sufficiently small so as to cause the microhooks 62 to push against one another thereby completely closing the device 20. The result of such the deployment is that depicted in FIG. 8. As shown, the peripheral surfaces 70 of the fabric 24 remain engaged with the adventitia 64 proximate the wound opening 54. In addition, the interior section 72 of the fabric 24 creates the closed end tube 65 extending away from the blood vessel wall 56 with the microhooks 62 thereon engaging one another. Moreover, the cinch ring 36 is pushed down against the exterior surface 66 of the blood vessel wall 56 which not only ensures closure, but given its dimensions, causes the blood vessel walls to pull together thereby shortening the width of the opening 54 as well.

Figure 8:
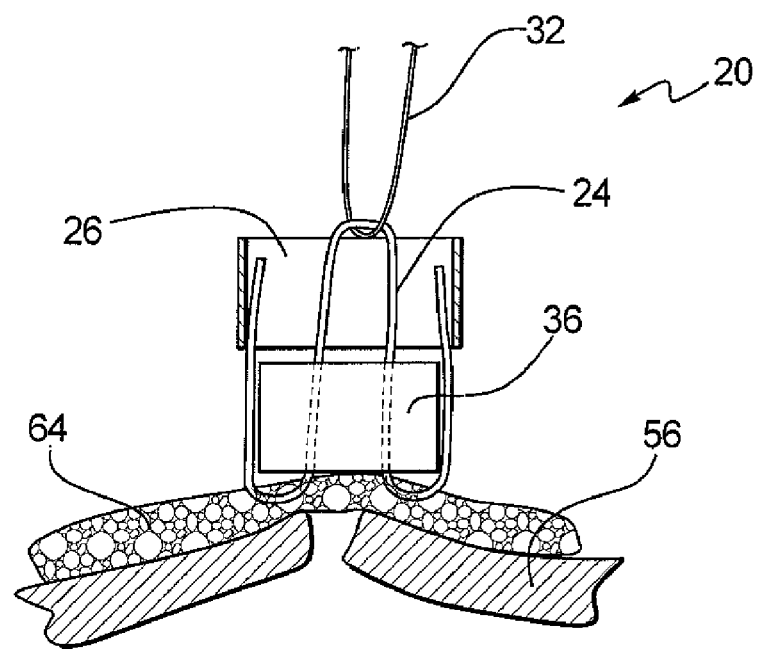
FIG. 8 is a schematic view depicting the suture retracted and the cinch ring being deployed.
Figure 9:
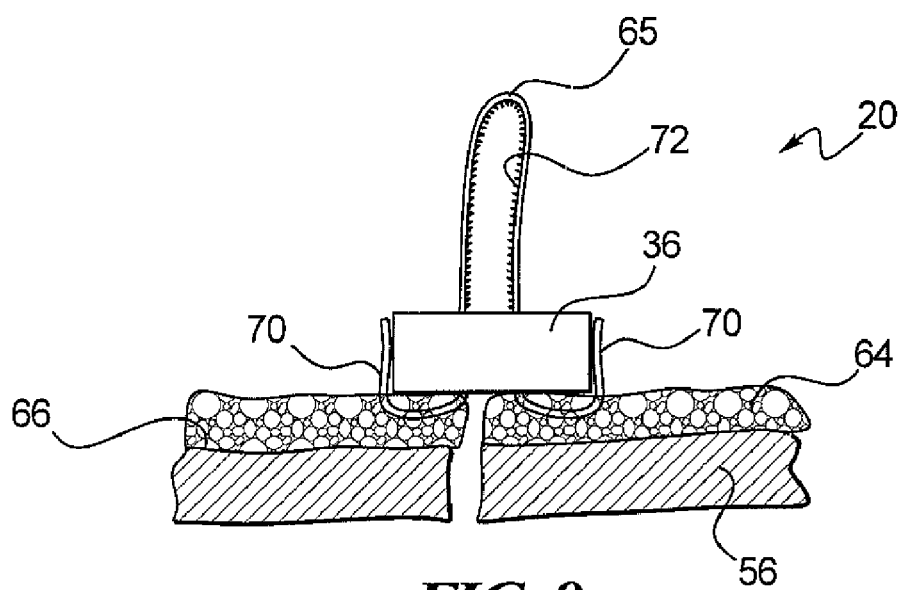
FIG. 9 is a schematic view showing the resulting closure device after the procedure has been completed.
Figure 10:
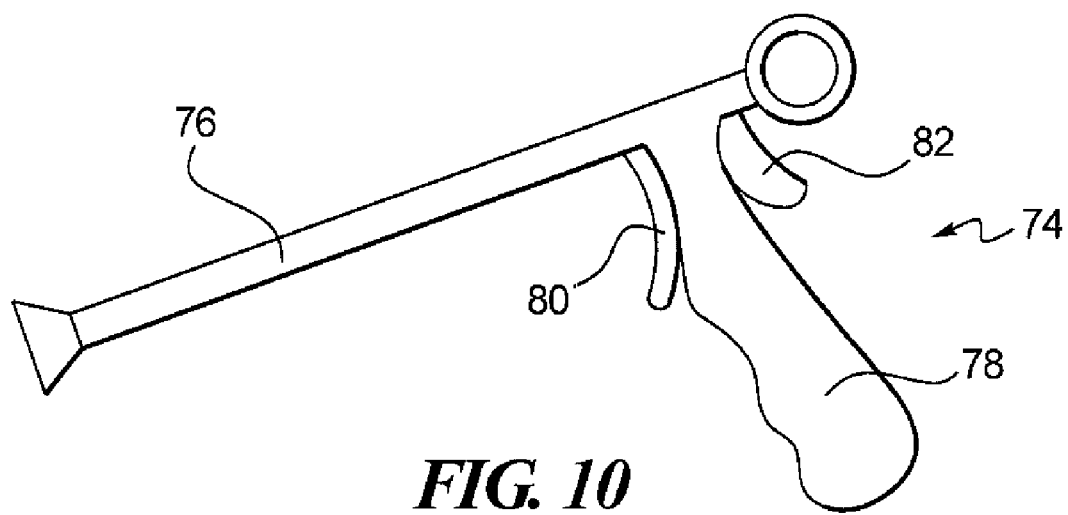
FIG. 10 is a perspective view depicting a deployment mechanism used with the wound closure device.

Referring now to FIG. 8, a deployment mechanism by which the device 20 can be deployed is generally referred to by reference numeral 74. As shown therein, the reference numeral 74 may take the form of a triggered gun or the like having the introducer sheath 26 forming a barrel 76 of the gun. A handle 78 may extend from the barrel 76 and include a trigger 80 as well as a lever 82. One or more additional actuation mechanisms may be provided as well. However, the trigger 80 and lever 82 may be used to simultaneously contract and retract the expandable frame 22, retract the suture 32, and deploy the cinch ring 36. By providing such mechanisms in a single medical device, the physician may be able to close the wound with a single hand.

Figure 11:
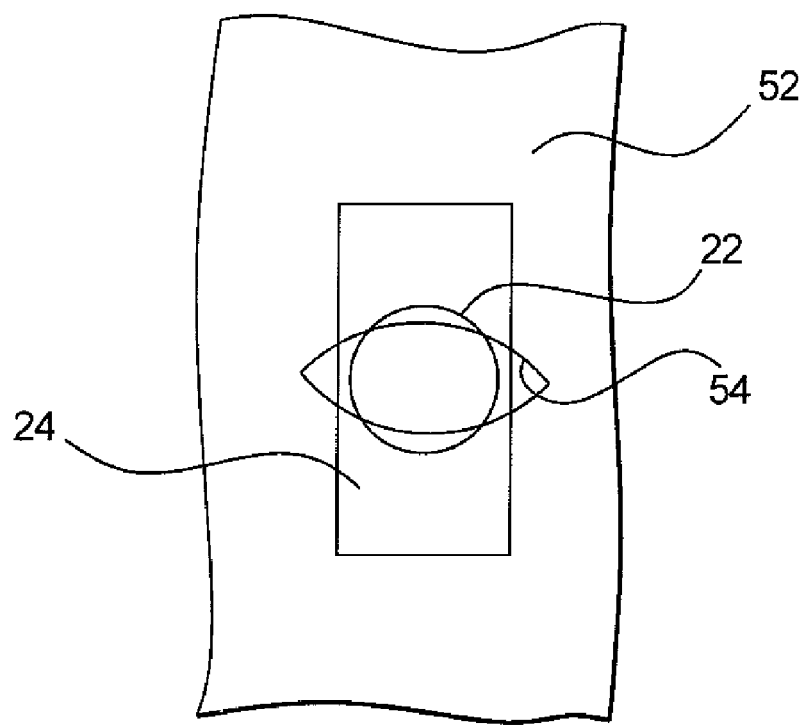
FIG. 11 is a plan view of an artery showing a top stick within the artery and the wound closure device deployed.

FIG. 11 depicts the blood vessel 52 in top or plan view. As shown therein, the expandable frame 22 and fabric 24 when deployed form a substantial rectangular shape extending across the opening 54. Accordingly, such a device would work most advantageously when the opening 54 is a "top stick" opening as shown, meaning the opening is provided generally in a top surface of the blood vessel 52. If a "sidestick" opening is made, alternative embodiments depicted in FIGS. 12 and 13 may advantageous employed. Such embodiments work substantially the same as the foregoing embodiment, but for their overall shape when deployed. As opposed to the first embodiment which is generally rectilinear in shape when deployed, the second embodiment has a ball-like or spherical shape when deployed. To achieve such a shape a spherical expander 122 and fabric sheath 124 may be employed. All other components are similar to the first embodiment and thus are similarly numbered but for a one hundred series prefix. With such an embodiment, the angle at which the device is introduced into the blood vessel is not of as much importance and thus the opening can be more easily closed even if it is a "sidestick" type opening.

With the embodiment depicted in FIG. 13, the deployed configuration shape is substantially conical. To achieve such a shape, a conically shaped expander 222 and fabric sheath 224 may be employed. The curved nature of such a shape has the "side-stick" benefits of the spherical embodiment, with the long tapered sides having the advantages of the first embodiment and its ability to grip and entangle with the adventitia. With each of the embodiments, the closure of the opening can be further augmented by appropriately rotating or twisting the device to ensure a proper grip between the microhooks and the adventitia.

From the foregoing, it can be seen that the present disclosure provides an apparatus and method for quickly and reliably closing a wound or opening in a blood vessel. The device uses a bioabsorbable material such as polylactic acid having a plurality of microhooks thereon to engage the adventitia surrounding the blood vessel. The entanglement between the microhooks and the adventitia is sufficiently strong so as to cause the fabric to remain deployed until hemostasis is reached. In addition, the device as disclosed is atraumatic to the surrounding tissue, is self-locating, and deploys in seconds resulting in quick, reliable closures.

What is claimed is:

1. A method of closing a wound, comprising:
   positioning a introducer sheath into a blood vessel;
   inserting a sealing assembly through the introducer sheath, the sealing assembly including an expandable frame surrounded by a tube of fabric, the tube of fabric having a closed distal end and a plurality of microhooks extending therefrom, the sealing assembly being inserted until the distal end of the tube of fabric extends from a distal end of the introducer sheath;
   expanding the expandable frame, the tube of fabric being expanded thereby as well;
   retracting the introducer sheath and sealing assembly until the introducer sheath is removed from the artery, the plurality of microhooks being engaged with adventitia surrounding the blood vessel thereby;
   contracting and removing the expandable frame;
   inverting the distal end of the tube of fabric; and
   sliding a cinch ring around the inverted distal end of the tube of fabric.

2. The method of claim 1, wherein the introducer sheath includes a bleed back port, and the introducer sheath being retracted until blood stops flowing through the port.

3. The method of claim 1, wherein the contracting, removing and inverting steps are performed simultaneously.

4. The method of claim 1, further including twisting the distal end of the tube of fabric after inverting the distal end.

5. The method of claim 1, wherein the tube of fabric and cinch ring are made of polylactic acid fiber.

6. The method of claim 1, wherein the distal end of the tube of fabric is inverted by retracting a suture connected to the distal end.

7. The method of claim 1, further including removing the introducer sheath, thereby leaving only the tube of fabric and the cinch ring in the wound.

* * * * *